US009956303B2

(12) United States Patent
Dalsgaard et al.

(10) Patent No.: US 9,956,303 B2
(45) Date of Patent: May 1, 2018

(54) ANTI-MET THERAPY FOR PREVIOUSLY DIAGNOSED CANCER PATIENTS

(71) Applicant: GE HEALTHCARE LIMITED, Little Chalfont (GB)

(72) Inventors: Grethe Tang Dalsgaard, Amersham (GB); Ian Andrew Wilson, Amersham (GB)

(73) Assignee: GE HEALTHCARE LIMITED (GB)

( * ) Notice: Subject to any disclaimer, the term of this patent is extended or adjusted under 35 U.S.C. 154(b) by 323 days.

(21) Appl. No.: 14/365,725

(22) PCT Filed: Dec. 19, 2012

(86) PCT No.: PCT/EP2012/076196
§ 371 (c)(1),
(2) Date: Jun. 16, 2014

(87) PCT Pub. No.: WO2013/092742
PCT Pub. Date: Jun. 27, 2013

(65) Prior Publication Data
US 2014/0335022 A1 Nov. 13, 2014

(30) Foreign Application Priority Data

Dec. 20, 2011 (GB) .................................. 1121914.4

(51) Int. Cl.
*A61K 49/00* (2006.01)
*C07K 14/475* (2006.01)
*G01N 33/50* (2006.01)
*G01N 33/574* (2006.01)
*A61K 51/08* (2006.01)
*A61K 39/395* (2006.01)
*A61K 45/06* (2006.01)
*C07K 16/28* (2006.01)

(52) U.S. Cl.
CPC ...... *A61K 49/0004* (2013.01); *A61K 39/3955* (2013.01); *A61K 45/06* (2013.01); *A61K 51/08* (2013.01); *C07K 14/4753* (2013.01); *C07K 16/2863* (2013.01); *G01N 33/5017* (2013.01); *G01N 33/574* (2013.01); *G01N 33/57423* (2013.01); *G01N 2800/52* (2013.01)

(58) Field of Classification Search
CPC ...... A61K 51/00; A61K 51/08; A61K 51/088; A61K 39/00; A61K 39/3955; A61K 45/00; A61K 45/06; A61K 49/00; A61K 49/0004; C07K 14/4753; C07K 16/2863; G01N 33/5017; G01N 33/574; G01N 33/57423; G01N 2800/52

USPC ......... 424/1.11, 1.65, 1.69, 1.81, 1.85, 1.89, 424/9.1, 9.2, 9.6; 514/1, 1.1, 19.2, 19.3, 514/19.4, 19.5, 19.6, 21.1, 21.4; 530/300, 530/317
See application file for complete search history.

(56) References Cited

U.S. PATENT DOCUMENTS

| 8,431,111 | B2 * | 4/2013 | Nairne ............. A61K 47/48238 424/1.11 |
| 8,529,874 | B2 * | 9/2013 | Johannesen ........ A61K 49/0032 424/1.11 |
| 8,568,693 | B2 | 10/2013 | Danikas et al. |
| 9,000,124 | B2 * | 4/2015 | Dransfield ....... A61K 47/48046 530/326 |
| 9,259,496 | B2 * | 2/2016 | Iveson .................. A61K 51/08 |
| 9,533,059 | B2 | 1/2017 | Iveson et al. |

FOREIGN PATENT DOCUMENTS

| EP | 2287197 | 2/2011 |
| EP | 2605802 A1 | 6/2013 |
| JP | 2011513211 A | 4/2011 |
| JP | 6014592 B2 | 10/2016 |
| WO | 2004/078778 | 9/2004 |
| WO | 2008/139207 | 11/2008 |
| WO | 2011/008990 | 1/2011 |
| WO | 2011/048029 | 4/2011 |
| WO | 2011048029 A1 | 4/2011 |
| WO | 2012/022676 A1 | 2/2012 |
| WO | 2013/092742 A1 | 6/2013 |

OTHER PUBLICATIONS

Garcia, et.al. British Journal of Cancer vol. 96, 2007, pp. 329-335.
GB1121914.4 Search Report dated Apr. 30, 2012.
PCT/EP2012/076196 ISRWO dated Mar. 28, 2013.
Office Action received for Japanese Patent Application No. 2014-547982, dated Jan. 17, 2017, 04 pages. (1 page English Communication + 3 pages Official Copy).
International Preliminary Report on Patentability received for PCT Patent Application No. PCT/EP2012/076196, dated Jun. 24, 2014, 8 pages.

* cited by examiner

*Primary Examiner* — D L Jones
(74) *Attorney, Agent, or Firm* — Wood IP LLC

(57) ABSTRACT

The present invention relates to methods useful in the selection of cancer patients suitable for treatment with therapies directed at c-Met. The method employs imaging agents which comprise $^{18}$F-radiolabelled c-Met binding peptides suitable for positron emission tomography (PET) imaging in vivo. Also disclosed are methods of treatment, methods of monitoring therapy directed atc-Met and the use of the imaging agents and peptides in the methods of the invention.

13 Claims, No Drawings

SEQUENCE LISTING

```
<160> NUMBER OF SEQ ID NOS: 7

<210> SEQ ID NO 1
<211> LENGTH: 17
<212> TYPE: PRT
<213> ORGANISM: Artificial
<220> FEATURE:
<223> OTHER INFORMATION: synthetic peptide
<220> FEATURE:
<221> NAME/KEY: DISULFID
<222> LOCATION: (1)..(13)
<220> FEATURE:
<221> NAME/KEY: VARIANT
<222> LOCATION: (2)..(2)
<223> OTHER INFORMATION: N, H or Y
<220> FEATURE:
<221> NAME/KEY: DISULFID
<222> LOCATION: (3)..(11)
<220> FEATURE:
<221> NAME/KEY: VARIANT
<222> LOCATION: (4)..(4)
<223> OTHER INFORMATION: G, S, T or N
<220> FEATURE:
<221> NAME/KEY: VARIANT
<222> LOCATION: (8)..(8)
<223> OTHER INFORMATION: T or R
<220> FEATURE:
<221> NAME/KEY: VARIANT
<222> LOCATION: (15)..(15)
<223> OTHER INFORMATION: A, D, E, G or S
<220> FEATURE:
<221> NAME/KEY: VARIANT
<222> LOCATION: (16)..(16)
<223> OTHER INFORMATION: S or T
<220> FEATURE:
<221> NAME/KEY: VARIANT
<222> LOCATION: (17)..(17)
<223> OTHER INFORMATION: D or E

<400> SEQUENCE: 1

Cys Xaa Cys Xaa Gly Pro Pro Xaa Phe Glu Cys Trp Cys Tyr Xaa Xaa
 1               5                  10                  15

Xaa

<210> SEQ ID NO 2
<211> LENGTH: 18
<212> TYPE: PRT
<213> ORGANISM: Artificial
<220> FEATURE:
<223> OTHER INFORMATION: synthetic peptide
<220> FEATURE:
<221> NAME/KEY: DISULFID
<222> LOCATION: (2)..(14)
<220> FEATURE:
<221> NAME/KEY: VARIANT
<222> LOCATION: (3)..(3)
<223> OTHER INFORMATION: N, H OR Y
<220> FEATURE:
<221> NAME/KEY: DISULFID
<222> LOCATION: (4)..(12)
<220> FEATURE:
<221> NAME/KEY: VARIANT
<222> LOCATION: (5)..(5)
<223> OTHER INFORMATION: G, S, T or N
<220> FEATURE:
<221> NAME/KEY: VARIANT
<222> LOCATION: (9)..(9)
<223> OTHER INFORMATION: T or R
<220> FEATURE:
<221> NAME/KEY: VARIANT
<222> LOCATION: (16)..(16)
<223> OTHER INFORMATION: A, D, E, G or S
```

```
<220> FEATURE:
<221> NAME/KEY: VARIANT
<222> LOCATION: (17)..(17)
<223> OTHER INFORMATION: S or T
<220> FEATURE:
<221> NAME/KEY: VARIANT
<222> LOCATION: (18)..(18)
<223> OTHER INFORMATION: D or E

<400> SEQUENCE: 2

Ser Cys Xaa Cys Xaa Gly Pro Pro Xaa Phe Glu Cys Trp Cys Tyr Xaa
1               5                   10                  15

Xaa Xaa

<210> SEQ ID NO 3
<211> LENGTH: 22
<212> TYPE: PRT
<213> ORGANISM: Artificial
<220> FEATURE:
<223> OTHER INFORMATION: synthetic peptide
<220> FEATURE:
<221> NAME/KEY: DISULFID
<222> LOCATION: (4)..(16)
<220> FEATURE:
<221> NAME/KEY: VARIANT
<222> LOCATION: (5)..(5)
<223> OTHER INFORMATION: N, H or Y
<220> FEATURE:
<221> NAME/KEY: DISULFID
<222> LOCATION: (6)..(14)
<220> FEATURE:
<221> NAME/KEY: VARIANT
<222> LOCATION: (7)..(7)
<223> OTHER INFORMATION: G, S, T or N
<220> FEATURE:
<221> NAME/KEY: VARIANT
<222> LOCATION: (11)..(11)
<223> OTHER INFORMATION: T or R
<220> FEATURE:
<221> NAME/KEY: VARIANT
<222> LOCATION: (18)..(18)
<223> OTHER INFORMATION: A, D, E, G or S
<220> FEATURE:
<221> NAME/KEY: VARIANT
<222> LOCATION: (19)..(19)
<223> OTHER INFORMATION: S or T
<220> FEATURE:
<221> NAME/KEY: VARIANT
<222> LOCATION: (20)..(20)
<223> OTHER INFORMATION: D or E

<400> SEQUENCE: 3

Ala Gly Ser Cys Xaa Cys Xaa Gly Pro Pro Xaa Phe Glu Cys Trp Cys
1               5                   10                  15

Tyr Xaa Xaa Xaa Gly Thr
            20

<210> SEQ ID NO 4
<211> LENGTH: 4
<212> TYPE: PRT
<213> ORGANISM: Artificial
<220> FEATURE:
<223> OTHER INFORMATION: synthetic peptide

<400> SEQUENCE: 4

Gly Gly Gly Lys
1

<210> SEQ ID NO 5
<211> LENGTH: 4
<212> TYPE: PRT
```

```
<213> ORGANISM: Artificial
<220> FEATURE:
<223> OTHER INFORMATION: synthetic peptide

<400> SEQUENCE: 5

Gly Ser Gly Lys
1

<210> SEQ ID NO 6
<211> LENGTH: 5
<212> TYPE: PRT
<213> ORGANISM: Artificial
<220> FEATURE:
<223> OTHER INFORMATION: synthetic peptide

<400> SEQUENCE: 6

Gly Ser Gly Ser Lys
1               5

<210> SEQ ID NO 7
<211> LENGTH: 26
<212> TYPE: PRT
<213> ORGANISM: Artificial
<220> FEATURE:
<223> OTHER INFORMATION: synthetic peptide
<220> FEATURE:
<221> NAME/KEY: DISULFID
<222> LOCATION: (4)..(16)
<220> FEATURE:
<221> NAME/KEY: DISULFID
<222> LOCATION: (6)..(14)

<400> SEQUENCE: 7

Ala Gly Ser Cys Tyr Cys Ser Gly Pro Pro Arg Phe Glu Cys Trp Cys
1               5                   10                  15

Tyr Glu Thr Glu Gly Thr Gly Gly Lys
            20                  25
```

ANTI-MET THERAPY FOR PREVIOUSLY DIAGNOSED CANCER PATIENTS

This application is a filing under 35 U.S.C. 371 of international application number PCT/EP2012/076196, filed Dec. 19, 2012, which claims priority to Great Britain application number 1121914.4 filed Dec. 20, 2011, the entire disclosure of which is hereby incorporated by reference.

FIELD OF THE INVENTION

The present invention relates to methods useful in the selection of cancer patients suitable for treatment with therapies directed at c-Met. The method employs imaging agents which comprise $^{18}$F-radiolabelled c-Met binding peptides suitable for positron emission tomography (PET) imaging in vivo. Also disclosed are methods of treatment, methods of monitoring therapy of c-Met and the use of the imaging agents and peptides in the methods of the invention.

BACKGROUND TO THE INVENTION

Hepatocyte growth factor (HGF), also known as scatter factor (SF), is a growth factor which is involved in various physiological processes, such as wound healing and angiogenesis. The high affinity interaction of HGF interaction with its receptor (c-Met) is implicated in tumour growth, invasion and metastasis.

Knudsen et al have reviewed the role of HGF and c-Met in prostate cancer, with possible implications for imaging and therapy [Adv. Cancer Res., 91, 31-67 (2004)]. Labelled anti-met antibodies for diagnosis and therapy are described in WO 03/057155, EP 2127683 A1 and WO 2011/110642.

c-Met has been shown to be involved in tumour growth, invasion and metastasis in many human cancers of epithelial origin. c-Met is expressed by most carcinomas and its elevated expression relative to normal tissue has been detected in cancers of: lung, breast, colorectal, pancreatic, head and neck, gastric, hepatocellular, ovarian, renal, glioma, melanoma and a number of sarcomas. In colorectal carcinoma (CRC), over-expression of c-Met has been detected in dysplastic aberrant crypt foci, the earliest preneoplastic lesions of the disease. In head and neck squamous cell cancer, c-Met is reportedly expressed or overexpressed in roughly 80% of primary tumours. In prostate cancer metastasis to bone, c-Met was reported overexpressed in over 80% of bone metastases.

Under normal conditions, c-Met is expressed on epithelial cells and activated in a paracrine fashion, by mesenchymally derived HGF. The activation of c-Met in normal cells is a transient event and is tightly regulated. In tumour cells, however, c-Met can be constitutively active. In cancer, aberrant c-Met stimulation can be achieved through c-Met amplification/over-expression, activating c-Met mutations (e.g. structural alterations) and acquisition of autonomous growth control through creation of autocrine signalling loops. In addition, a defective down-regulation of the c-Met receptor will also contribute to aberrant c-Met expression in the cell membrane. While the over-expression of c-Met is HGF dependent (autocrine/paracrine), structural alterations caused by mutations are HGF independent (e.g. loss of extracellular domain).

WO 2004/078778 discloses polypeptides or multimeric peptide constructs which bind c-Met or a complex comprising c-Met and HGF. Approximately 10 different structural classes of peptide are described. WO 2004/078778 discloses that the peptides can be labelled with a detectable label for in vitro and in vivo applications, or with a drug for therapeutic applications. The detectable label can be: an enzyme, a fluorescent compound, an optical dye, a paramagnetic metal ion, an ultrasound contrast agent or a radionuclide. Preferred labels of WO 2004/078778 are stated to be radioactive or paramagnetic, and most preferably comprise a metal which is chelated by a metal chelator. WO 2004/078778 states that the radionuclides therein can be selected from: $^{18}$F, $^{124}$I, $^{125}$I, $^{131}$I, $^{123}$I, $^{77}$Br, $^{76}$Br, $^{99m}$Tc, $^{51}$Cr, $^{67}$Ga, $^{68}$Ga, $^{47}$Sc, $^{167}$Tm, $^{141}$Ce, $^{111}$In, $^{168}$Yb, $^{175}$Yb, $^{140}$La, $^{90}$Y, $^{88}$Y, $^{153}$Sm, $^{166}$Ho, $^{165}$Dy, $^{166}$Dy, $^{62}$Cu, $^{64}$Cu, $^{67}$Cu, $^{97}$Ru, $^{103}$Ru, $^{186}$Re, $^{203}$Pb, $^{211}$Bi, $^{212}$Bi, $^{213}$Bi, $^{214}$Bi, $^{105}$Rh, $^{109}$Pd, $^{117}$Sn, $^{149}$Pm, $^{161}$Tb, $^{177}$Lu, $^{198}$Au and $^{199}$Au. WO 2004/078778 states (page 62) that the preferred radionuclides for diagnostic purposes are: $^{64}$Cu, $^{67}$Ga, $^{68}$Ga, $^{99m}$Tc and $^{111}$In, with $^{99m}$Tc being particularly preferred.

WO 2008/139207 discloses c-Met binding cyclic peptides of 17 to 30 amino acids which are labelled with an optical reporter imaging moiety suitable for imaging the mammalian body in vivo using light of green to near-infrared wavelength 600-1200 nm. The c-Met binding peptides comprise the amino acid sequence:

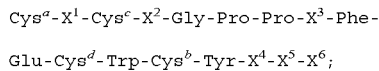

wherein X$^1$ is Asn, His or Tyr;
X$^2$ is Gly, Ser, Thr or Asn;
X$^3$ is Thr or Arg;
X$^4$ is Ala, Asp, Glu, Gly or Ser;
X$^5$ is Ser or Thr;
X$^6$ is Asp or Glu;
and Cys$^{a-d}$ are each cysteine residues such that residues a and b as well as c and d are cyclised to form two separate disulfide bonds. The optical reporter of WO 2008/139207 is preferably a cyanine dye.

WO 2009/016180 discloses c-Met binding cyclic peptides analogous to those of WO 2008/139207, wherein the optical reporter is a benzopyrylium dye. The agents of WO 2008/139207 and WO 2009/016180 are stated to be useful for in vitro and in vivo optical applications, especially optical imaging in vivo of the human body. Optical imaging of colorectal cancer is a preferred application.

WO 2011/020925 discloses anti-c-Met antibodies and uses thereof. WO 2011/020925 discloses that the antibodies can be used to help determine the susceptibility of a patient to treatment with anti-c-Met antibodies. The method involves the use of an in vitro method (immunohistochemical analysis of a tumour sample) to determine the c-Met status of a tumour. This method still, however, relies on biopsy with the disadvantages described above.

Merchant et al [2011 ASCO Meeting; J. Clin. Oncol., Abstract 10632, Suppl. (2011)] disclose an anti-c-Met antibody (MetMab™) labelled with $^{76}$Br or $^{89}$Zr— for molecular imaging of c-Met in mouse xenografts. The agents were reported to exhibit rapid tumour uptake and slow clearance.

Drug chemotherapeutic agents directed at c-Met ("anti-Met therapies") are in development by a number of organisations. Such agents are expected to be used typically in metastatic disease. Clinical results to date, however, suggest that patient prognosis is dependent on knowledge of the c-Met status of the tumour. It is also possible that c-Met status could be predictive of response to anti-c Met therapies. Currently, the c-Met status can be determined by immunohistochemical (IHC) analysis of a biopsy sample taken from the patient, but biopsy is invasive (carrying some risk to the patient), and may not result in a representative sample. Thus, there is an inherent risk of sampling error where mainly healthy tissue is collected, or due to tumour heterogeneity, a section of the tumour that is unrepresentative of the molecular profile for the most active part of the tumour is taken [N. Engl. J. Med., 366(10); 883-892 (2012)]. In addition, biopsy provides information only on the tumour sampled—not the patient's tumour and/or tumour metastasis burden as a whole. Since anti-Met therapy is expected to be used as a second- or third-line therapy, biopsy material of satisfactory quality representative of the untreated tumour may be unavailable, or could potentially no longer be representative for the molecular profile of the tumour. Resampling via biopsy is generally not carried out, as it carries some risk of morbidity, as well as due to the issues described above.

In a recently published study [Cancer Discovery, 1(1); 44-53 (2011)], the value of obtaining new biopsies in pre-treated NSCLC patients with advanced disease (n=139) and utilizing real-time biomarker analyses for selection of treatment was explored. It was found that allocating patients to treatment based on the molecular profile increased the probability of a positive treatment outcome. Though the biopsy procedure reportedly was well-tolerated in the trial, pneumothorax occurred in 11.5% of the patients, leading to the conclusion that although re-biopsying patients for treatment stratification based on biomarkers is advantageous, it is not without risk.

In a Phase II trial for MetMAb™, a monoclonal antibody blocking c-Met (Roche) [2011 ASCO Annual Meeting & http://www.roche.com/media/media_releases/med-cor-2011-05-19.htm], NSCLC patients were randomised to either:
  (i) MetMAb+Erlotinib (EGFR inhibitor; or
  (ii) placebo+Erlotinib.
c-Met status was determined by IHC and FISH analyses of archive samples (approximately 50% were positive by IHC). In the patient group as a whole (i.e. including patients with high and low c-Met expression), there were no differences between the two treatments. When the data were analysed, based on retrospective IHC analysis of archive biopsy samples, the median overall-survival was 12.6 months in the MetMAb group vs 3.8 months in the Erlotinib group (p=0.002). In addition, the patients with low c-Met expression treated with MetMAb in combination with Erlotinib had a worse outcome compared to Erlotinib alone. Prospective collection of biopsies prior to treatment was not included in the trial, and it is unknown if the c-Met scoring based on the archive samples was fully representative for the study population. Oliner et al. [J Clin Oncol 30, Suppl., abstr 4005 (2012)] recently published data for a Phase 2 study of the HGF antibody, rilotumumab (Amgen), in combination with epirubicin, cisplatin, and capecitabine (ECX) in patients with locally advanced or metastatic gastric or esophagogastric junction cancer. Patients with c-Met high tumours (>50% tumour cells positive) had improved median overall survival when treated with the combination therapy compared to patients treated with placebo and ECX. Conversely, patients with c-Met low tumours (≤50% positive) had a trend toward unfavourable overall survival when treated with the combination therapy compared with those treated with placebo and ECX. In the placebo and ECX group, patients with c-Met high tumours had poorer overall than patients with c-Met low tumours.

There is therefore a need for a less invasive method of assessing the c-Met status of the tumour and/or tumour metastasis burden of a patient, to determine whether the individual patient would benefit from anti-Met therapy.

The Present Invention.

The present invention provides a method of determining the c-Met status of patient's tumour(s), to assist in the decision process before initiation of c-Met therapy in cancers such as, NSCLC, colorectal cancer (CRC) and gastric cancer. For anti-Met therapy, a treating physician would need to know the c-Met status of the patient (tumour and metastases) before initiating adjuvant c-Met inhibitor therapy. For a newly diagnosed patient it may be possible to get the answer from molecular analysis of the diagnostic biopsy, but for patients that have failed on standard therapy, if any archive sample is available it may not be fully representative of the current status of the disease.

The method of the present invention assists the physician in determining when an individual patient would benefit from anti-Met therapy. Importantly, the method also helps to exclude from such treatment patients where anti-Met therapy would either be ineffective, or have a negative effect.

The method of the present invention carries much less risk to the patient than biopsy, and has the advantage of providing a way of assessing total c-Met burden for all tumours and metastases—including e.g. the expression of tumour sites that are difficult to biopsy, or sites of previously unknown metastasis. It therefore gives a more complete picture for the patient than analysis of biopsy samples (even assuming such samples are available). In addition, the method lends itself to repeat imaging at different time intervals, so can be used to monitor anti-Met therapy.

MetMab™ exhibits a combined elimination half-life of 8-12 days, so does not have ideal pharmacokinetics for in vivo imaging—since clearance from background would be extremely slow. In contrast, the agents of the present invention permit imaging within 1 hour of administration to the patient.

The present invention also provides a means for monitoring anti-Met therapy. This is expected to be of significance in either determining that a given therapy is proving successful for an individual patient (and is hence worth continuing), or is not efficacious—permitting an earlier change to a different treatment or medication.

DETAILED DESCRIPTION OF THE INVENTION

In a first aspect, the present invention provides a method to assist in the determination of whether an individual patient previously diagnosed with cancer, is susceptible to treatment with anti-Met therapy, said method comprising:
  (i) provision of an imaging agent which comprises an $^{18}$F-radio labelled c-Met binding cyclic peptide;
  (ii) imaging at least one site of said cancer with the imaging agent of step (i), wherein said imaging agent had been previously administered to said patient;
  (iii) making a determination from the imaging of step (ii) whether or not there is elevated uptake of said imaging agent at said site;
  (iv) when the determination of step (iii) shows elevated uptake, the cancer is deemed to overexpress c-Met, and anti-Met therapy is determined to be suitable for said patient;
  (v) when the determination from step (iii) shows no elevated uptake, the cancer is deemed not to overexpress c-Met, and anti-Met therapy is determined not to be suitable for said patient;

wherein said c-Met binding cyclic peptide is an 18 to 30-mer cyclic peptide of Formula I:

  (I)

where:
cMBP is of Formula II:

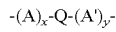  (II)

where Q is the amino acid sequence (SEQ-1):
-Cys$^a$-X$^1$-Cys$^c$-X$^2$-Gly-Pro-Pro-X$^3$-Phe-Glu-Cys$^d$-Trp-Cys$^b$-Tyr-X$^4$-X$^5$-X$^6$-
wherein X$^1$ is Asn, His or Tyr;
X$^2$ is Gly, Ser, Thr or Asn;
X$^3$ is Thr or Arg;
X$^4$ is Ala, Asp, Glu, Gly or Ser;
X$^5$ is Ser or Thr;
X$^6$ is Asp or Glu;
and Cys$^{a-d}$ are each cysteine residues such that residues a and b as well as c and d are cyclised to form two separate disulfide bonds;
A and A' are independently any amino acid other than Cys, with the proviso that at least one of A and A' is present and is Lys;
x and y are independently integers of value 0 to 13, and are chosen such that [x+y]=1 to 13;
Z$^1$ is attached to the N-terminus of cMBP, and is H or M$^{IG}$;
Z$^2$ is attached to the C-terminus of cMBP and is OH, OB$^c$, or M$^{IG}$,
where B$^c$ is a biocompatible cation;
each M$^{IG}$ is independently a metabolism inhibiting group which is a biocompatible group which inhibits or suppresses in vivo metabolism of the cMBP peptide;
wherein cMBP is labelled at the Lys residue of the A or A' groups with $^{18}$F.

The term "c-Met" has its conventional meaning, and refers to the Hepatocyte growth factor (HGF) receptor—also known as MET. HGF is also known as scatter factor (SF).

The term "patient" refers to a mammal, preferably the intact mammalian body in vivo, and more preferably a human subject. By the phrase "previously diagnosed with cancer" is meant that the patient has already been positively diagnosed with cancer and preferably the location of at least the primary site(s) of cancer in that individual patient are known. This diagnosis can be carried out by methods known in the art. The phrase also includes pre-cancerous lesions, where the clinical diagnosis is that the lesion will develop into a cancer, and may benefit from treatment with anti-Met therapy.

By the phrase "susceptible to treatment" is meant that the individual patient is suffering from a form of cancer wherein the treatment will prolong life expectancy and/or reduce the impact of the cancerous condition on the wellbeing of the patient. The overall benefit:risk ratio of taking the medication for that individual patient is thus positive (i.e. beneficial)

By the term "anti-Met therapy" is meant chemotherapy wherein a medication is delivered to the patient which comprises an agent which inhibits HGF/c-Met signalling through: direct inhibition of the receptor (eg. an anti-c-Met antibody); through inactivation of its ligand HGF (eg. AMG102, L2G7); by interfering with HGF binding to c-Met (eg. NK4); or by inhibiting c-Met kinase activity (eg. PHA-665752 and SU11274). The medication may be delivered by any suitable route of administration. As used herein, the term "anti-Met therapy" excludes external beam radiotherapy. Preferred such therapies are described in the second aspect (below).

By the term "imaging agent" is meant a compound suitable for in vivo imaging of the mammalian body. Preferably, the mammal is an intact mammalian body in vivo, and is more preferably a human subject. Preferably, the imaging agent can be administered to the mammalian body in a minimally invasive manner, i.e. without a substantial health risk to the mammalian subject when carried out under professional medical expertise. Such minimally invasive administration is preferably intravenous administration into a peripheral vein of said subject, without the need for local or general anaesthetic. The term "in vivo imaging" as used herein refers to those techniques that non-invasively produce images of all or part of an internal aspect of a mammalian subject.

By the term "previously administered" is meant that the step involving the clinician, wherein the imaging agent is given to the mammalian subject already been carried out prior to imaging.

By the term "elevated uptake" means that the target:background ratio for signal from the imaging agent taken up in the region of interest of the cancer relative to such signal in the adjoining tissue background is positive. A minimum such ratio is 1.1:1 with respect to tumour:muscle or tumour:blood ratio.

By the term "c-Met binding cyclic peptide" is meant a peptide which binds to the hepatocyte growth factor receptor, also known as c-Met (or simply MET). Suitable such peptides of the present invention are cyclic peptides of 18 to 30 amino acids of Formula I. Such peptides have an apparent K$_D$ for c-Met of less than about 20 nM. The cMBP sequence of said peptides comprises proline residues, and it is known that such residues can exhibit cis/trans isomerisation of the backbone amide bond. The cMBP peptides of the present invention include any such isomers.

The Z$^1$ group substitutes the amine group of the last amino acid residue of the cMBP, i.e., the amino terminus Thus, when Z$^1$ is H, the amino terminus of the cMBP terminates in a free NH$_2$ group of the last amino acid residue. The Z$^2$ group substitutes the carbonyl group of the last amino acid residue of the cMBP—i.e. the carboxy terminus. Thus, when Z$^2$ is OH, the carboxy terminus of the cMBP terminates in the free CO$_2$H group of the last amino acid residue, and when Z$^2$ is OB$^c$ that terminal carboxy group is ionised as a CO$_2$B$^c$ group.

By the term "biocompatible cation" (B$^c$) is meant a positively charged counterion which forms a salt with an ionised, negatively charged group, where said positively charged counterion is also non-toxic and hence suitable for administration to the mammalian body, especially the human body. Examples of suitable biocompatible cations include: the alkali metals sodium or potassium; the alkaline earth metals calcium and magnesium; and the ammonium ion. Preferred biocompatible cations are sodium and potassium, most preferably sodium.

By the term "metabolism inhibiting group" (M$^{IG}$) is meant a biocompatible group which inhibits or suppresses in vivo metabolism of the cMBP peptide at either the amino terminus (Z$^1$) or carboxy terminus (Z$^2$). Such groups are well known to those skilled in the art and are suitably chosen from, for the peptide amine terminus: N-acylated groups —NH(C=O)R$^G$ where the acyl group —(C=O)R$^G$ has R$^G$ chosen from: C$_{1-6}$ alkyl, or C$_{3-10}$ aryl groups or comprises a polyethyleneglycol (PEG) building block. For the peptide carboxy terminus: carboxamide, tert-butyl ester, benzyl ester, cyclohexyl ester, amino alcohol or a polyethyleneglycol (PEG) building block. Preferred such PEG groups are the biomodifiers of Formula IA or IB:

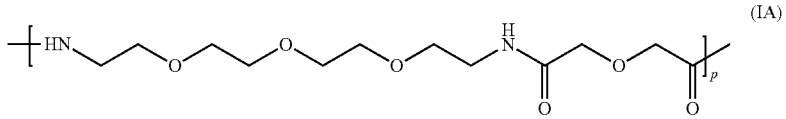

17-amino-5-oxo-6-aza-3,9,12,15-tetraoxaheptadecanoic acid of Formula IA
wherein p is an integer from 1 to 10. Alternatively, a PEG-like structure based on a propionic acid derivative of Formula IB can be used:

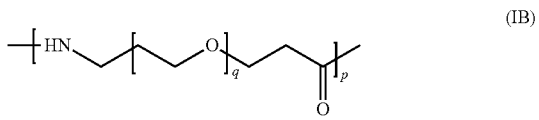

where p is as defined for Formula IA and
q is an integer from 3 to 15.

In Formula IB, p is preferably 1 or 2, and q is preferably 5 to 12.

Preferred such amino terminus $M^{IG}$ groups are acetyl, benzyloxycarbonyl or trifluoroacetyl, most preferably acetyl.

By the term "$^{18}$F-radiolabelled" is meant that the c-Met binding cyclic peptide has covalently conjugated thereto the radioisotope $^{18}$F. The $^{18}$F is suitably attached via a C—F fluoroalkyl or fluoroaryl bond, since such bonds are relatively stable in vivo, and hence confer resistance to metabolic cleavage of the $^{18}$F radiolabel from the cMBP peptide. The $^{18}$F is preferably attached via a C—F fluoroaryl bond. The $^{18}$F may be attached directly to one of the amino acids of the cMBP, but is preferably conjugated as part of a radio fluorinated substituent on the cMBP. Said substituents are preferably of formula:

-(L)$_n$-$^{18}$F where:
L is a synthetic linker group of formula -(A)$_m$- wherein each A is independently —CR$_2$—, —CR═CR—, —C≡C—, —CR$_2$CO$_2$—, —CO$_2$CR$_2$—, —NR(C═O)—, —(C═O)NR—, —NR(C═O)NR—, —NR(C═S)NR—, —SO$_2$NR—, —NRSO$_2$—, —CR$_2$OCR$_2$—, —CR$_2$SCR$_2$—, —CR$_2$NRCR$_2$—, —CR$_2$—O—N═, —CR$_2$—O—NR—, —CR$_2$—O—NH(CO)—, a C$_{4-8}$ cycloheteroalkylene group, a C$_{4-5}$ cycloalkylene group, a C$_{5-12}$ arylene group, or a C$_{3-12}$ heteroarylene group, an amino acid, a sugar or a monodisperse polyethyleneglycol (PEG) building block; each R is independently chosen from H, C$_{1-4}$ alkyl, C$_{2-4}$ alkenyl, C$_{2-4}$ alkynyl, C$_{1-4}$ alkoxyalkyl or C$_{1-4}$ hydroxyalkyl;
m is an integer of value 1 to 20;
n is an integer of value 0 or 1.

By the term "amino acid" is meant an L- or D-amino acid, amino acid analogue (eg. naphthylalanine) or amino acid mimetic which may be naturally occurring or of purely synthetic origin, and may be optically pure, i.e. a single enantiomer and hence chiral, or a mixture of enantiomers. Conventional 3-letter or single letter abbreviations for amino acids are used herein. Preferably the amino acids of the present invention are optically pure. By the term "amino acid mimetic" is meant synthetic analogues of naturally occurring amino acids which are isosteres, i.e. have been designed to mimic the steric and electronic structure of the natural compound. Such isosteres are well known to those skilled in the art and include but are not limited to depsipeptides, retro-inverso peptides, thioamides, cycloalkanes or 1,5-disubstituted tetrazoles [see M. Goodman, Biopolymers, 24, 137, (1985)].

By the term "peptide" is meant a compound comprising two or more amino acids, as defined above, linked by a peptide bond (i.e. an amide bond linking the amine of one amino acid to the carboxyl of another).

By the term "sugar" is meant a mono-, di- or tri-saccharide. Suitable sugars include:

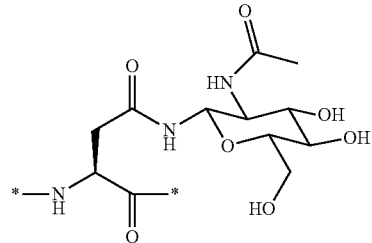 [SMILES: *N[C@@H](CC(=O)NC1OC(CO)C(O)C(O)C1NC(C)=O)C(*)=O]

glucose, galactose, maltose, mannose, and lactose. Optionally, the sugar may be functionalised to permit facile coupling to amino acids. Thus, eg. a glucosamine derivative of an amino acid can be conjugated to other amino acids via peptide bonds. The glucosamine derivative of asparagine (commercially available from NovaBiochem) is one example of this:

When A and A' are "any amino acid other than Cys" that means that the additional amino acid of the A and A' groups lack free thiol groups, in particular Cys residues. That is because an additional Cys residue would risk disulfide bridge scrambing with the Cys$^a$-Cys$^b$ and Cys$^c$-Cys$^d$ disulfide bridges of the Q sequence, with consequent loss or reduction of c-Met binding affinity.

Preferred Features.

In the method of the first aspect, the cancer is preferably non-small cell lung cancer (NSCLC), colorectal cancer, gastric cancer, pancreatic cancer, head and neck cancer, ovarian cancer, breast cancer, melanoma, glioma or sarcoma, or other cancers of epithelial origin. The tumour of the cancer is preferably a solid tumour. More preferably, the cancer is NSCLC, colorectal cancer or gastric cancer. Most preferably, the cancer is NSCLC.

Preferred cMBP peptides of the present invention have a $K_D$ for binding of c-Met to c-Met/HGF complex of less than about 10 nM (based on fluorescence polarisation assay measurements), most preferably in the range 1 to 5 nM, with less than 3 nM being the ideal.

The cMBP peptide of Formulae I and II is preferably of Formula IIA:

-(A)$_x$-Q-(A')$_z$-Lys-    (IIA)

wherein A is as defined for Formula II, z is an integer of value 0 to 12, and [x+z]=0 to 12, and cMBP comprises only one Lys residue.

Thus, in Formula IIA the single Lys residue is located specifically at the C-terminus of the cMBP. That in turn means that the $^{18}$F radiolabel is preferably located at the C-terminus position.

Q preferably comprises the amino acid sequence of either SEQ-2 or SEQ-3:

```
Ser-Cysᵃ-X¹-Cysᶜ-X²-Gly-Pro-Pro-X³-Phe-Glu-    (SEQ-2)

Cysᵈ-Trp-Cysᵇ-Tyr-X⁴-X⁵-X⁶;
```

```
Ala-Gly-Ser-Cysᵃ-X¹-Cysᶜ-X²-Gly-Pro-Pro-X³-    (SEQ-3)

Phe-Glu-Cysᵈ-Trp-Cysᵇ-Tyr-X⁴-X⁵-X⁶-Gly-Thr.
```

In SEQ-1, SEQ-2 and SEQ-3, X³ is preferably Arg. In Formula I and Formula II, the -(A)$_x$- or -(A')$_y$- groups preferably comprise a linker peptide which is chosen from:

```
-Gly-Gly-Gly-Lys-,    (SEQ-4)

-Gly-Ser-Gly-Lys-    (SEQ-5)
or

-Gly-Ser-Gly-Ser-Lys-.    (SEQ-6)
```

The cMBP peptide of the first aspect preferably has the amino acid sequence (SEQ-7):

```
Ala-Gly-Ser-Cysᵃ-Tyr-Cysᶜ-Ser-Gly-Pro-

Pro-Arg-Phe-Glu-Cysᵈ-Trp-Cysᵇ-Tyr-Glu-

Thr-Glu-Gly-Thr-Gly-Gly-Gly-Lys.
```

Preferred imaging agents of the present invention have both cMBP peptide termini protected by M$^{IG}$ groups, i.e. preferably both Z$^1$ and Z$^2$ are M$^{1G}$, which will usually be different. Having both peptide termini protected in this way is important for in vivo imaging applications, since otherwise rapid peptide metabolism would be expected with consequent loss of selective binding affinity for c-Met. When both Z$^1$ and Z$^2$ are M$^{IG}$, preferably Z$^1$ is acetyl and Z$^2$ is a primary amide. Most preferably, Z$^1$ is acetyl and Z$^2$ is a primary amide and the $^{18}$F moiety is attached to the epsilon amine side chain of a lysine residue of cMBP.

The radio fluorinated substituent -(L)$_n$-$^{18}$F may be attached to the alpha amino group of the N-terminus of the c-Met binding peptide, or alternatively to the amine side chain of any amino-substituted amino acids (e.g. Lys residues). Preferably, it is attached to the epsilon (ε) amine group of the Lys residue of the cMBP.

Preferred radio fluorinated substituents -(L)$_n$-$^{18}$F have n=1, i.e. a synthetic linker group as defined above is present.

More preferred such substituents comprise the $^{18}$F radiolabel bound to a phenyl group, i.e. the substituent is of formula:

-(A)$_x$C$_6$H$_4$-$^{18}$F where: A is as defined above,
x is an integer of value 0 to 5.

Most preferred such substituents arise from either N-acylation of the Lys amine residue with a fluorinated active ester, or condensation of an amino-oxy derivative of the Lys amine residue with a fluorinated benzaldehyde, and are of formula:

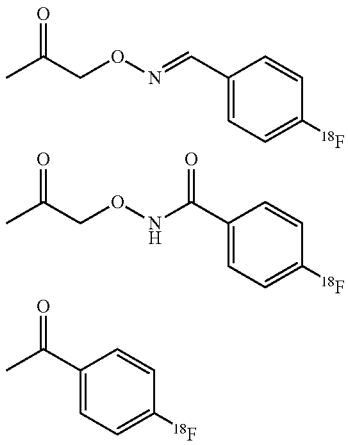

The imaging agent of the first aspect is preferably provided as an imaging agent composition which comprises:
(i) the $^{18}$F-radiolabelled c-Met binding cyclic peptide as defined in the first aspect;
(ii) an unlabelled c-Met binding cyclic peptide;
wherein: said c-Met binding cyclic peptide has the same amino acid sequence in (i) and (ii),
and wherein the unlabelled cMBP peptide is present in said composition at no more than 50 times the molar amount of said $^{18}$F-labelled cMBP peptide.

Preferred embodiments of the $^{18}$F-radiolabelled c-Met binding cyclic peptide in the composition are as described above. The term "composition" has its conventional meaning, i.e. a mixture of the specified components. The composition may be in solid or liquid/solution form.

By the term "unlabelled" is meant that the c-Met binding cyclic peptide is non-radioactive, i.e. is not radiolabelled with $^{18}$F, or any other radioisotope. One or more such peptides may be present in the composition, and such unlabelled peptides primarily include the non-radioactive precursors of the fourth aspect (below). The term 'unlabelled' excludes the c-Met binding cyclic peptide labelled with $^{19}$F, where said $^{19}$F is present in the $^{18}$F-fluoride used to radiolabel said c-Met binding cyclic peptide and is thus a product of the same radiolabelling reaction. As is known in the art, if two fluorine-substituted compounds differ only in the isotopes of the fluorine atom, they would behave chemically in an almost identical manner, and hence their separation would be extremely difficult. The unlabelled c-Met binding cyclic peptide or precursor preferably has the groups Z$^1$ and/or Z$^2$ already attached.

Preferably, the unlabelled c-Met binding cyclic peptide is present in said composition at up to 30, more preferably up to 20, most preferably less than 10 times the molar amount of the corresponding $^{18}$F-labelled peptide. The composition is preferably in solution form, wherein the components (i) and (ii) are both present in solution. More preferably, the solution is a biocompatible solvent, or mixture of two or more such solvents. Preferred such biocompatible solvents are described below, and preferably comprises an aqueous solvent.

The imaging agent of the first aspect is preferably provided as a pharmaceutical composition which comprises said imaging agent together with a bio compatible carrier, in a sterile form suitable for mammalian administration. The "biocompatible carrier" is a fluid, especially a liquid, in which the imaging agent can be suspended or preferably dissolved, such that the composition is physiologically tolerable, i.e. can be administered to the mammalian body without toxicity or undue discomfort. The biocompatible carrier is suitably an injectable carrier liquid such as sterile, pyrogen-free water for injection; an aqueous solution such as saline (which may advantageously be balanced so that the final product for injection is isotonic); an aqueous buffer solution comprising a biocompatible buffering agent (e.g. phosphate buffer); an aqueous solution of one or more tonicity-adjusting substances (eg. salts of plasma cations with biocompatible counterions), sugars (e.g. glucose or sucrose), sugar alcohols (eg. sorbitol or mannitol), glycols (eg. glycerol), or other non-ionic polyol materials (eg. polyethyleneglycols, propylene glycols and the like). Preferably the biocompatible carrier is pyrogen-free water for injection, isotonic saline or phosphate buffer. Use of a buffer is preferred in order to control pH. Preferably, the composition is maintained at pH at or above 7.5, optionally with 5-10% v/v ethanol as solubiliser. The pharmaceutical composition may contain additional optional excipients such as: an antimicrobial preservative, pH-adjusting agent, filler, radioprotectant, solubiliser or osmolality adjusting agent.

A most preferred imaging agent composition of the present invention comprises the cMBP peptide of SEQ-7 having $Z^1=Z^2=M^{IG}$ attached, and a combination of para-aminobenzoic acid radioprotectant and ethanol radioprotectant/solubiliser in aqueous buffer. A preferred peptide of SEQ-7 in such preferred compositions is Peptide 1, and a preferred $^{18}$F-labelled cMBP peptide is Compound 3. The radioactive concentration is preferably less than 350 MBq/ml, with a pABA concentration of 2 mg/ml, and ethanol at about 5-10% vol/vol, preferably 6.5-7.5% vol/vol.

The imaging agents and biocompatible carrier are each supplied in suitable vials or vessels which comprise a sealed container which permits maintenance of sterile integrity and/or radioactive safety, plus optionally an inert headspace gas (eg. nitrogen or argon), whilst permitting addition and withdrawal of solutions by syringe or cannula.

The pharmaceutical compositions may be prepared under aseptic manufacture (i.e. clean room) conditions to give the desired sterile, non-pyrogenic product. It is preferred that the key components, especially the associated reagents plus those parts of the apparatus which come into contact with the imaging agent (eg. vials) are sterile. The components and reagents can be sterilised by methods known in the art, including: sterile filtration, terminal sterilisation using e.g. gamma-irradiation, autoclaving, dry heat or chemical treatment (e.g. with ethylene oxide). It is preferred to sterilise some components in advance, so that the minimum number of manipulations needs to be carried out. As a precaution, however, it is preferred to include at least a sterile filtration step as the final step in the preparation of the pharmaceutical composition.

The imaging agents of the first aspect can be prepared by radio fluorination of a suitable precursor. Such a precursor comprises:
(i) the c-Met binding cyclic peptide of Formula I wherein $Z^1=Z^2=M^{IG}$; or
(ii) an amino-oxy functionalised c-Met binding cyclic peptide.

By the term "amino-oxy functionalised c-Met binding cyclic peptide" is meant the c-Met binding cyclic peptide of Formula I having covalently conjugated thereto an amino-oxy functional group. Such amino-oxy groups are of formula —O—NH$_2$, preferably —CH$_2$O—NH$_2$ and have the advantage that the amine of the amino-oxy group is more reactive than a Lys amine group in condensation reactions with aldehydes to form oxime ethers. Such amino-oxy groups are suitably attached at the Lys residue of the cMBP, as described below.

The precursor is non-radioactive, and is designed so that it can be obtained in a high degree of chemical purity. It is also designed so that, upon reaction with a suitable source of $^{18}$F, reaction occurs efficiently with satisfactory radiochemical purity (RCP). The "suitable source of $^{18}$F" depends on the nature of the precursor. When the precursor comprises the unlabelled c-Met binding peptide of Formula I, the amine group of the lysine (Lys) residue of the unlabelled peptide is designed to be the site of radiolabelling. The termini of the cMBP peptide are protected, since $Z^1=Z^2=M^{IG}$. Preferred such c-Met binding peptides and preferred $Z^1/Z^2$ groups are as described in the first aspect. Thus, the suitable source of $^{18}$F is designed to react as efficiently as possible with the lysine amine group, preferably the Lys epsilon amine.

For the preparation of a pharmaceutical composition, the precursor is preferably in sterile form, more preferably a lyophilised solid. The precursor is preferably an amino-oxy functionalised c-Met binding peptide.

c-Met binding peptides of Formula I, i.e. $Z^1$-[cMBP]-$Z^2$ of the present invention may be obtained by a method of preparation which comprises:
(i) solid phase peptide synthesis of a linear peptide which has the same peptide sequence as the desired cMBP peptide and in which the Cys$^a$ and Cys$^b$ are unprotected, and the Cys$^c$ and Cys$^d$ residues have thiol-protecting groups;
(ii) treatment of the peptide from step (i) with aqueous base in solution to give a monocyclic peptide with a first disulphide bond linking Cys$^a$ and Cys$^b$;
(iii) removal of the Cys$^c$ and Cys$^d$ thiol-protecting groups and cyclisation to give a second disulphide bond linking Cys$^c$ and Cys$^d$, which is the desired bicyclic peptide product $Z^1$-[cMBP]-$Z^2$.

By the term "protecting group" is meant a group which inhibits or suppresses undesirable chemical reactions, but which is designed to be sufficiently reactive that it may be cleaved from the functional group in question under mild enough conditions that do not modify the rest of the molecule. After deprotection the desired product is obtained. Amine protecting groups are well known to those skilled in the art and are suitably chosen from: Boc (where Boc is tert-butyloxycarbonyl), Fmoc (where Fmoc is fluorenylmethoxycarbonyl), trifluoroacetyl, allyloxycarbonyl, Dde [i.e. 1-(4,4-dimethyl-2,6-dioxocyclohexylidene)ethyl] or Npys (i.e. 3-nitro-2-pyridine sulfenyl). Suitable thiol protecting groups are Trt (Trityl), Acm (acetamidomethyl), t-Bu (tert-butyl), tert-Butylthio, methoxybenzyl, methylbenzyl or Npys (3-nitro-2-pyridine sulfenyl). The use of further protecting groups are described in 'Protective Groups in Organic Synthesis', 4$^{th}$ Edition, Theorodora W. Greene and Peter G. M. Wuts, [Wiley Blackwell, (2006)]. Preferred amine protecting groups are Boc and Fmoc, most preferably Boc. Preferred amine protecting groups are Trt and Acm.

Examples 1 and 2 provide further specific details. Further details of solid phase peptide synthesis are described in P. Lloyd-Williams, F. Albericio and E. Girald; *Chemical Approaches to the Synthesis of Peptides and Proteins*, CRC Press, 1997. The cMBP peptides are best stored under inert atmosphere and kept in a freezer. When used in solution, it is best to avoid pH above 7 since that risks scrambling of the disulfide bridges.

Amino-oxy functionalised c-Met binding peptides can be prepared by the methods of Poethko et al [J. Nucl. Med., 45, 892-902 (2004)], Schirrmacher et al [Bioconj. Chem., 18, 2085-2089 (2007)], Solbakken et al [Bioorg. Med. Chem. Lett, 16, 6190-6193 (2006)] or Glaser et al [Bioconj. Chem., 19, 951-957 (2008)]. The amino-oxy group may optionally be conjugated in two steps. First, the N-protected amino-oxy carboxylic acid or N-protected amino-oxy activated ester is conjugated to the c-Met binding peptide. Second, the intermediate N-protected amino-oxy functionalised c-Met binding peptide is deprotected to give the desired product (see Solbakken and Glaser papers cited above). N-protected amino-oxy carboxylic acids such as Boc-NH—O—CH$_2$(C=O)OH are commercially available, e.g. from Novabiochem.

The $^{18}$F-radiolabelled c-Met binding cyclic peptides can be prepared as follows:
  (i) provision of the precursor as described above;
  (ii) when said precursor comprises an unlabelled c-Met binding cyclic peptide of Formula I wherein $Z^1=Z^2=M^{IG}$, reaction with either an $^{18}$F-labelled activated ester, or an $^{18}$F-labelled carboxylic acid in the presence of an activating agent, to give the $^{18}$F-radiolabelled c-Met binding cyclic peptide conjugated via an amide linkage at the Lys residue of the cMBP of said cyclic peptide;
  (iii) when said precursor comprises an amino-oxy functionalised c-Met binding cyclic peptide, reaction with either:
    (a) an $^{18}$F-labelled activated ester, or an $^{18}$F-labelled carboxylic acid in the presence of an activating agent, to give the $^{18}$F-radiolabelled c-Met binding cyclic peptide conjugated via an amide linkage at the amino-oxy position of said functionalised peptide; or
    (b) an $^{18}$F-labelled aldehyde to give the $^{18}$F-radiolabelled c-Met binding cyclic peptide conjugated via an oxime ether linkage at the amino-oxy position of said functionalised peptide.

By the term "activated ester" or "active ester" is meant an ester derivative of the associated carboxylic acid which is designed to be a better leaving group, and hence permit more facile reaction with nucleophile, such as amines. Examples of suitable active esters are: N-hydroxysuccinimide (NHS); sulfo-succinimidyl ester; pentafluorophenol; pentafluorothiophenol; para-nitrophenol; hydroxybenzotriazole and PyBOP (i.e. benzotriazol-1-yl-oxytripyrrolidinophosphonium hexafluorophosphate). Preferred active esters are N-hydroxysuccinimide or pentafluorophenol esters, especially N-hydroxysuccinimide esters.

By the term "activating agent" is meant a reagent used to facilitate coupling between an amine and a carboxylic acid to generate an amide. Suitable such activating agents are known in the art and include carbodiimides such as EDC [N-(3-dimethylaminopropyl)-N-ethylcarbodiimide and N,N'-dialkylcarbodiimides such as dicyclohexylcarbodiimide or diisopropylcarbodiimide; and triazoles such as HBTU [O-(benzotriazol-1-yl)-N,N,N',N'-tetramethyluronium hexafluorophosphate], HATU [O-(7-azabenzotriazol-1-yl)-N,N,N',N'-tetramethyluronium hexafluorophosphate], and PyBOP [benzotriazol-1-yloxy)tripyrrolidinophosphonium hexafluorophosphate]. Further details are given in *"March's Advanced Organic Chemistry"*, 5$^{th}$ Edition, pages 508-510, Wiley Interscience (2001). A preferred such activating agent is EDC.

$^{18}$F-labelled activated esters, such as [$^{18}$F]SFB can be prepared by the method of Glaser et al, and references therein [J. Lab. Comp. Radiopharm., 52, 327-330 (2009)], or the automated method of Marik et al [Appl. Rad. Isot., 65(2), 199-203 (2007)]:

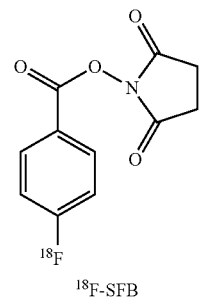

$^{18}$F-SFB $^{18}$F-labelled carboxylic acids can be obtained by the method of Marik et al cited above. $^{18}$F-labelled aliphatic aldehydes of formula $^{18}$F(CH$_2$)$_2$O[CH$_2$CH$_2$O]$_q$CH$_2$CHO, where q is 3, can be obtained by the method of Glaser et al [Bioconj. Chem., 19(4), 951-957 (2008)]. $^{18}$F-fluorobenzaldehyde can be obtained by the method of Glaser et al [J. Lab. Comp. Radiopharm., 52, 327-330 (2009)]. The precursor Me$_3$N$^+$—C$_6$H$_4$—CHO. CF$_3$SO$_3^-$ is obtained by the method of Haka et al [J. Lab. Comp. Radiopharm., 27, 823-833 (1989)].

The conjugation of $^{18}$F-labelled aldehydes to amino-oxy functionalised c-Met peptides is preferably carried out in the presence of an aniline catalyst as described by Flavell et al [J. Am. Chem. Soc., 130(28), 9106-9112 (2008)]. Whilst it is possible to use protected amino-oxy c-Met peptides (such as Compound 1) as precursors, the free amino-oxy derivative (such as Compound 2) is preferred. That is because the whole synthesis is more amenable to automation, whereas with the protected precursor, a manual deprotection step is typically required.

The preferred imaging agent composition can be obtained as follows:
  (i) preparing the $^{18}$F-radiolabelled c-Met binding cyclic peptide;
  (ii) chromatographic separation of the unlabelled c-Met binding cyclic peptide from the $^{18}$F-radiolabelled c-Met binding cyclic peptide.

The chromatographic separation of step (ii) may be carried out by HPLC or SPE (solid phase extraction) using one or more SPE cartridge(s). SPE is preferred when an automated synthesizer is used, and HPLC is preferred in other circumstances. Example 5 provides a suitable HPLC method for Compound 3 of the present invention.

When the imaging agent is provided as a pharmaceutical composition, the method reparation is preferably carried out using an automated synthesizer apparatus. By the term "automated synthesizer" is meant an automated module based on the principle of unit operations as described by Satyamurthy et al [Clin. Positr. Imag., 2(5), 233-253 (1999)]. The term 'unit operations' means that complex processes are reduced to a series of simple operations or reactions, which can be applied to a range of materials. Such automated synthesizers are preferred for the method of the present invention especially when a radiopharmaceutical composition is desired. They are commercially available from a range of suppliers [Satyamurthy et al, above], including: GE Healthcare; CTI Inc; Ion Beam Applications S.A. (Chemin du Cyclotron 3, B-1348 Louvain-La-Neuve, Belgium); Raytest (Germany) and Bioscan (USA).

In a second aspect, the present invention provides a method of treatment of an individual patient previously diagnosed with cancer, said method comprising:

(i) carrying out the method of determination of the first aspect;

(ii) when the determination of step (i) is that anti-Met therapy is suitable for said patient, then anti-Met therapy for said patient is either initiated or continued.

Preferred aspects of the imaging agent and the method of determination in the second aspect are as described in the first aspect (above).

The term "anti-Met therapy" is as defined in the first aspect (above). The anti-Met therapy preferably comprises:

(a) a non-proteinaceous c-Met inhibitor;

(b) an anti-Met antibody or fragment thereof;

(c) an anti-HGF antibody or fragment thereof;

(d) a drug that indirectly affects the c-Met signalling pathway; or combinations thereof.

The term "non-proteinaceous" has its conventional meaning. Preferred such c-Met inhibitors are synthetic. The term "synthetic" has its conventional meaning, i.e. man-made as opposed to being isolated from natural sources e.g. from the mammalian body. Such compounds have the advantage that their manufacture and impurity profile can be fully controlled. The c-Met inhibitor is preferably a "small molecule", i.e. has a molecular weight of less than 2000 Daltons, more preferably less than 1500 Daltons, mots preferably less than 1000 Daltons.

By the phrase "drug that indirectly affects the c-Met signalling pathway" is meant a pharmacologically active compound which interferes with the c-Met signalling pathway, either upstream or downstream, in such a way as to have an inhibitory/antagonistic or an agonistic effect on c-Met regulation, expression or function. Examples of drugs which would indirectly affect transcription of the Apc gene and the downstream expression of c-Met are: β-catenin inhibitors or NFκB/IKK inhibitors. Further details are of anti-Met therapies are provided by Toschi et al [Clin. Cancer Res., 14(19), 5941-5946 (2008)]. Two anti-Met therapies have been approved (crizotinib and cabozantinib), and more are currently in clinical development (based on http://clinicaltrials.gov/ct2/search and abstracts at various scientific meetings) are as follows:

| Compound | Company | Comment |
| --- | --- | --- |
| Xalkori ®/Crizotinib/ PF-02341066 | Pfizer | First-line treatment for NSCLC w. ALK-mutation |
| Cabozantinib/XL-184/ BMS-907351 | Exelixis/Bristol-Myers-Squibb | Effect on c-Met/RET/VEGFR$_2$ |
| Tivantinib/ARQ-197 | Arqule/Daiichi Sankyo/Kyowa Hakko | Small molecule, stabilise inactive conformation of c-Met. |
| Rilotumumab/AMG 102 | Amgen | Human mAb that blocks the action of HGF. |

| Compound | Company | Comment |
| --- | --- | --- |
| MetMAb/ PRO143966 | Genentech | Humanized mAb that blocks the action of HGF. |
| Foretinib/ GSK1363089/(XL-880) | GSK | Effect on: c-Met/AXL/ VEGFR$_2$ |
| MGCD-265 | MethylGene | Effect on: c-MetNEGFR$_{1,2,3}$/ Tie-2/Ron. |
| E7050 | Eisai Inc. | Effect on: c-Met/VEGFR$_2$ |
| Ficlatuzumab/ SCH900105/AV299 | AVEO Pharmaceuticals Inc/Schering-Plough | anti-HGF mAb |
| INCB028060/INC280 | Incyte Corporation/ Novartis | Small molecule c-Met inhibitor |
| AMG 208 | Amgen | Small molecule c-Met inhibitor |
| EMD 1214063 | EMD Serono | Small molecule c-Met inhibitor |
| EMD 1204831 | EMD Serono | Small molecule c-Met inhibitor |
| SAR125844 | Sanofi-Aventis | Small molecule c-Met inhibitor |
| AMG 337 | Amgen | Small molecule c-Met inhibitor |
| LY-2801653 | Eli Lilly | Small molecule c-Met inhibitor |
| Amuvatinib/MP-470 | SuperGen | Multi-targeted TK-inhibitor & RAD51 suppressor |
| PF-04217903 | Pfizer | c-Met Kinase inhibitor |
| BMS-777607 | Bristol-Myers Squibb | Small molecule c-Met inhibitor |
| MK-2461 | Merck | ATP-compet. Multi-targeted inhibitor of activated c-Met |
| MK-8033 | Merck | Small molecule c-MET inhibitor |
| JNJ-38877605 | Johnson & Johnson/Ortho Biotech | Selective Met Inhibitor |
| TAK-701 | Millennium Pharmaceuticals, Inc. | Humanized anti-HGF mAb |

Crizotinib is now on the market in some countries.

In the second aspect, the anti-Met therapy may optionally be delivered as part of a combination therapy with an additional treatment, where the additional treatment is chosen from:

(i) an EGFR inhibitor;

(ii) a tyrosine kinase inhibitor;

(iii) a VEGF inhibitor;

(iv) standard cancer chemotherapy drugs;

(v) a β-catenin inhibitor.

In a third aspect, the present invention provides a method of monitoring the therapy of an individual patient previously diagnosed with cancer and previously treated with the anti-Met therapy as defined in the second aspect, wherein said method comprises carrying out the imaging and determination of steps (ii) and (iii) respectively of the first aspect at one or more time intervals after initiation of said therapy.

Preferred embodiments of the imaging agent and determination in the third aspect are as described in the first aspect (above). Preferred embodiments of the anti-Met therapy in the third aspect are as described in the second aspect (above).

In the method of monitoring of the third aspect, it is anticipated that multiple, images of the region(s) of interest of the patient's cancer will be carried out. Comparative imaging techniques are known in the art, such as image subtraction and/or analysis of tumour:background ratios at different time points can then be used to assist in the determination of whether the degree of c-Met overexpression has changed in response to either anti-Met therapy, or other therapies that may affect c-Met expression (e.g. up-regulation of c-Met in patients failing on erlotinib in non-small cell lung cancer [Cappuzz et al. Annal. Oncol., 20:

298-304 (2009); Engelman, et al. Science 316, 1039-1043 (2007)], and up-regulation of c-Met in response to ionizing radiation leading to radioresistance [De Bacco et al., J. Natl. Cancer Inst., 103(8), 645-61 (2011)]. Patient management can then be changed in terms of e.g. continuation of therapy; change in dosage; change to a different anti-Met therapy; initiation of combination therapy, elective surgery or termination of the course of therapy.

A baseline scan measuring in-vivo expression of c-Met followed by a second scan within one month of the initiation of therapy has the potential to be indicative of the ultimate response to therapy as assessed at a later time point by measuring tumor size. The hypothesis is that a sharp fall in c-Met expression after the start of therapy is predictive of therapy response. The clinical utility of this could be to reduce time and money spent on administration of a futile therapy. Thus, sequential scans have the potential to provide an early signal that the anti c-Met therapy is failing to sustain an anti-tumor effect. In that instance, the lack of change (or possibly rise) in c-Met expression has the potential to accurately and reliably predict failure of the therapy. This could be of great clinical utility, since it would facilitate an early switch to an alternative therapy that could prove more efficacious.

In a fourth aspect, the present invention provides the use of the $^{18}$F-radio labelled c-Met binding cyclic peptide as defined in the first aspect in the method of determination of the first aspect; the method of treatment of the second aspect, or the method of monitoring of the third aspect.

Preferred aspects of the $^{18}$F-radiolabelled c-Met binding cyclic peptide in the fourth aspect are as described in the first aspect (above).

In a fifth aspect, the present invention provides the use of the c-Met binding cyclic peptide of Formula (I) as defined in the first aspect, in the method of determination of the first aspect; the method of treatment of the second aspect, or the method of monitoring of the third aspect.

Preferred aspects of the c-Met binding cyclic peptide and method of determination in the fifth aspect are as described in the first aspect (above). Preferred aspects of the method of treatment in the fifth aspect are as described in the second aspect (above). Preferred aspects of the method of monitoring in the fifth aspect are as described in the third aspect (above).

In a sixth aspect, the present invention provides the use of the anti-Met therapy as defined in the second aspect, in the method of treatment of the second aspect, or the method of monitoring of the third aspect.

Preferred aspects of the anti-Met therapy in the sixth aspect are as described in the first aspect (above).

The invention is illustrated by the non-limiting Examples detailed below. Example 1 provides the synthesis of a cMBP peptide of the invention having metabolism inhibiting groups ($Z^1=Z^2=M^{IG}$) at both termini (Peptide 1). Example 2 provides the synthesis of a protected precursor of the invention (Compound 1). Example 3 provides the synthesis of the non-radioactive, fluorinated (i.e. $^{19}$F) counterpart of the fluorine-labelled c-Met peptide (Compound 3A). Example 4 provides the synthesis of an $^{18}$F-radiofluorinated c-Met peptide of the invention (Compound 3B). Example 5 provides HPLC conditions for the separation of labelled and unlabelled c-Met binding peptides.

Example 6 provides the biodistribution of an $^{18}$F-labelled peptide of the invention (Compound 3B) in an animal tumour model. The results show binding to the human c-Met receptor expressed in the HT-29 tumours, and hence utility for tumour imaging. Example 7 demonstrates that the tumour uptake of Example 6 is specific, since the uptake can be inhibited by co-administration of non-radioactive $^{19}$F-labelled c-Met binding peptide (Compound 3A).

Example 8 also demonstrates reduced liver uptake of about 40% in primates when $^{19}$-labelled c-Met binding peptide is co-administered. Co-administration of a $^{19}$F-labelled scrambled version of the peptide, which has no affinity for the c-Met receptor, did not significantly reduce the liver uptake. The liver has a high level of c-Met expression, and the reduction in uptake following competition with $^{19}$F-labelled cMBP is therefore believed to represent evidence of specific c-Met binding in vivo.

Example 9 provides the automated synthesis of Compound 3B, further including automated use of SPE cartridge purification. The results show that Compound 3B can be obtained in high purity and satisfactory radiochemical yield using this approach. Example 10 describes human imaging using an imaging agent of the invention.

Abbreviations

Conventional single letter or 3-letter amino acid abbreviations are used.
% id: percentage injected dose
Ac: Acetyl
Acm: Acetamidomethyl
ACN: Acetonitrile
Boc: tert-Butyloxycarbonyl
DCM: Dichloromethane
DIPEA: N,N-Diisopropylethyl amine
DMF: Dimethylformamide
DMSO: Dimethylsulfoxide
EDC: N-3-dimethylaminopropyl)-N'-ethylcarbodiimide.
Fmoc: 9-Fluorenylmethoxycarbonyl
HBTU: O-Benzotriazol-1-yl-N,N,N',N'-tetramethyluronium hexafluorophosphate
HPLC: High performance liquid chromatography
HSPyU O—(N-succinimidyl)-N,N,N',N'-tetramethyleneuronium hexafluorophosphate
NHS: N-hydroxy-succinimide
NMM: N-Methylmorpholine
NMP: 1-Methyl-2-pyrrolidinone
pABA: para-aminobenzoic acid.
Pbf: 2,2,4,6,7-Pentamethyldihydrobenzofuran-5-sulfonyl
PBS: Phosphate-buffered saline
p.i.: post-injection
PyBOP: benzotriazol-1-yl-oxytripyrrolidinophosphonium hexafluorophosphate
SPE: solid phase extraction.
SUV: standard uptake values.
tBu: tert-butyl
TFA: Trifluoroacetic acid
TIS: Triisopropylsilane
Trt: Trityl.

| Compounds of the Invention. | |
|---|---|
| Name | Structure |
| Peptide 1 | Disulfide bridges at Cys4-16 and Cys6-14; Ac-Ala-Gly-Ser-Cys-Tyr-Cys-Ser-Gly-Pro-Pro-Arg-Phe-Glu-Cys-Trp-Cys-Tyr-Glu-Thr-Glu-Gly-Thr-Gly-Gly-Gly-Lys-NH$_2$, or Ac-AGSCYCSGPPRFECWCYETEGTGGGK-NH$_2$ |

Compounds of the Invention.

| Name | Structure |
|---|---|
| Compound 1 | 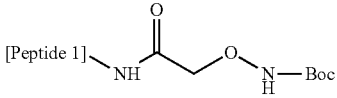 |
| Compound 2 | 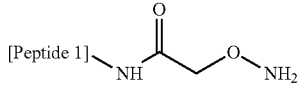 |
| Compound 3 | 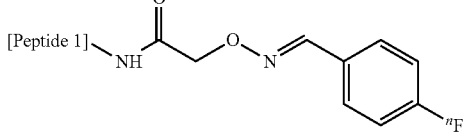<br>n = 19 Compound 3A;<br>n = 18 Compound 3B. | where:
Compounds 1, 2 and 3 are functionalised at the epsilon amine group of the carboxy terminal Lys of Peptide 1; Boc = tert-Butyloxycarbonyl.

Example 1: Synthesis of Peptide 1

Step (a): Synthesis of Protected Precursor Linear Peptide

The precursor linear peptide has the structure:

```
Ac-Ala-Gly-Ser-Cys-Tyr-Cys(Acm)-Ser-Gly-
Pro-Pro-Arg-Phe-Glu-Cys(Acm)-Trp-Cys-Tyr-
Glu-Thr-Glu-Gly-Thr-Gly-Gly-Gly-Lys-NH₂
```

The peptidyl resin H-Ala-Gly-Ser(tBu)-Cys(Trt)-Tyr(tBu)-Cys(Acm)-Ser(tBu)-Gly-Pro-Pro-Arg(Pbf)-Phe-Glu(OtBu)-Cys(Acm)-Trp(Boc)-Cys(Trt)-Tyr(tBu)-Glu(OtBu)-Thr($\psi^{Me,Me}$pro)-Glu(OtBu)-Gly-Thr(tBu)-Gly-Gly-Gly-Lys(Boc)-Polymer was assembled on an Applied Biosystems 433A peptide synthesizer using Fmoc chemistry starting with 0.1 mmol Rink Amide Novagel resin. An excess of 1 mmol pre-activated amino acids (using HBTU) was applied in the coupling steps. Glu-Thr pseudoproline (Novabiochem 05-20-1122) was incorporated in the sequence. The resin was transferred to a nitrogen bubbler apparatus and treated with a solution of acetic anhydride (1 mmol) and NMM (1 mmol) dissolved in DCM (5 mL) for 60 min. The anhydride solution was removed by filtration and the resin washed with DCM and dried under a stream of nitrogen.

The simultaneous removal of the side-chain protecting groups and cleavage of the peptide from the resin was carried out in TFA (10 mL) containing 2.5% TIS, 2.5% 4-thiocresol and 2.5% water for 2 hours and 30 min. The resin was removed by filtration, TFA removed in vacuo and diethyl ether added to the residue. The formed precipitate was washed with diethyl ether and air-dried affording 264 mg of crude peptide.

Purification by preparative HPLC (gradient: 20-30% B over 40 min where A=H₂O/0.1% TFA and B=ACN/0.1% TFA, flow rate: 10 mL/min, column: Phenomenex Luna 5µ C18 (2) 250×21.20 mm, detection: UV 214 nm, product retention time: 30 min) of the crude peptide afforded 100 mg of pure Peptide 1 linear precursor. The pure product was analysed by analytical HPLC (gradient: 10-40% B over 10 min where A=H₂O/0.1 TFA and B=ACN/0.1% TFA, flow rate: 0.3 mL/min, column: Phenomenex Luna 3µ C18 (2) 50×2 mm, detection: UV 214 nm, product retention time: 6.54 min). Further product characterisation was carried out using electrospray mass spectrometry ($MH_2^{2+}$ calculated: 1464.6, $MH_2^{2+}$ found: 1465.1).

Step (b): Formation of Monocyclic Cys4-16 Disulfide Bridge

```
Cys4-16;
Ac-Ala-Gly-Ser-Cys-Tyr-Cys(Acm)-Ser-Gly-
Pro-Pro-Arg-Phe-Glu-Cys(Acm)-Trp-Cys-Tyr-
Glu-Thr-Glu-Gly-Thr-Gly-Gly-Gly-Lys-NH₂.
```

The linear precursor from step (a) (100 mg) was dissolved in 5% DMSO/water (200 mL) and the solution adjusted to pH 6 using ammonia. The reaction mixture was stirred for 5 days. The solution was then adjusted to pH 2 using TFA and most of the solvent removed by evaporation in vacuo. The residue (40 mL) was injected in portions onto a preparative HPLC column for product purification.

Purification by preparative HPLC (gradient: 0% B for 10 min, then 0-40% B over 40 min where A=H₂O/0.1% TFA and B=ACN/0.1% TFA, flow rate: 10 mL/min, column: Phenomenex Luna 5µ C18 (2) 250×21.20 mm, detection: UV 214 nm, product retention time: 44 min) of the residue afforded 72 mg of pure Compound 1 monocyclic precursor.

The pure product (as a mixture of isomers P1 to P3) was analysed by analytical HPLC (gradient: 10-40% B over 10 min where A=H₂O/0.1% TFA and B=ACN/0.1% TFA, flow rate: 0.3 mL/min, column: Phenomenex Luna 3µ C18 (2) 50×2 mm, detection: UV 214 nm, product retention time: 5.37 min (P1); 5.61 min (P2); 6.05 min (P3)). Further product characterisation was carried out using electrospray mass spectrometry ($MH_2^{2+}$ calculated: 1463.6, $MH_2^{2+}$ found: 1464.1 (P1); 1464.4 (P2); 1464.3 (P3)).

Step (c): Formation of Second Cys6-14 Disulfide Bridge (Peptide 1)

The monocyclic precursor from step (b) (72 mg) was dissolved in 75% AcOH/water (72 mL) under a blanket of nitrogen. 1 M HCl (7.2 mL) and 0.05 M I₂ in AcOH (4.8 mL) were added in that order and the mixture stirred for 45 min. 1 M ascorbic acid (1 mL) was added giving a colourless mixture. Most of the solvents were evaporated in vacuo and the residue (18 mL) diluted with water/0.1% TFA (4 mL) and the product purified using preparative HPLC.

Purification by preparative HPLC (gradient: 0% B for 10 min, then 20-30% B over 40 min where A=H₂O/0.1 TFA and B=ACN/0.1% TFA, flow rate: 10 mL/min, column: Phenomenex Luna 5µ C18 (2) 250×21.20 mm, detection: UV 214 nm, product retention time: 43-53 min) of the residue afforded 52 mg of pure Peptide 1. The pure product was analysed by analytical HPLC (gradient: 10-40% B over 10 min where A=H₂O/0.1% TFA and B=ACN/0.1% TFA, flow rate: 0.3 mL/min, column: Phenomenex Luna 3µ C18 (2) 50×2 mm, detection: UV 214 nm, product retention time: 6.54 min). Further product characterisation was carried out using electrospray mass spectrometry ($MH_2^{2+}$ calculated: 1391.5, $MH_2$ found: 1392.5).

Example 2: Synthesis of Compound 1

(Boc-aminooxy)acetic acid (Sigma-Aldrich; 138 mg, 0.72 mmol), EDC (138 mg, 0.72 mmol) and N-hydroxysuccinimide (83 mg, 0.72 mmol) were dissolved in DMF (1 ml). The solution was shaken for 25 min, and then added to a solution of Peptide 1 (1.0 g, 0.36 mmol) in DMF (5 ml). The reaction mixture was stirred for 2 min. Sym.-collidine (239 µL, 1.80 mmol) was then added, and the reaction mixture stirred for 3 hours. The reaction mixture was diluted with water (5 ml), and the product purified by preparative RP-HPLC.

HPLC conditions: Waters Prep 4000 system, Solvent A=$H_2O$/0.1% TFA and Solvent B=ACN/0.1% TFA; gradient 20-40% B over 60 min; flow rate=50 ml/min; column: Phenomenex Luna 10 µm C18 (2) 250×50 mm; detection: uv 214 nm. Yield of purified Compound 1 690 mg (65%). Found m/z: 1478.4, expected $MH_2^{2+}$: 1478.1.

Example 3: Synthesis of Compound 3A

Step (a): Preparation of N-(4-fluorobenzylidene)aminooxyacetic acid (Boc-aminooxy)acetic acid (96 mg, 0.50 mmol) and 4-fluorobenzaldehyde (53 µL, 0.50 mmol) were dissolved in formic acid (0.5 ml), and the reaction mixture stirred for 135 mins. The reaction mixture was then diluted with 20% ACN/water/0.1% TFA (7 ml), and the product purified by semi-preparative RP-HPLC.

HPLC conditions: Beckman System Gold; Solvent A=$H_2O$/0.1% TFA and Solvent B=ACN/0.1% TFA; gradient 25-35% B over 40 min; flow rate=10 ml/min; column: Phenomenex Luna 5 µm C18 (2) 250×21.2 mm; detection: uv 214 nm.

Yield 92 mg (93%).

Step (b): Preparation of Compound 3A

N-(4-Fluorobenzylidene)aminooxyacetic acid [from Step (a), 43 mg, 0.22 mmol] and PyBOP (112 mg, 0.22 mmol) were dissolved in DMF (2 ml). A solution of DIPEA (157 µL, 0.90 mmol) in DMF (10 ml) was added, and the mixture shaken for 1 min. The solution was then added to a solution of Peptide 1 (500 mg, 0.18 mmol) in DMF (10 ml), and the reaction mixture shaken for 30 min. The reaction mixture was then diluted with water (20 ml), and the product purified by preparative HPLC.

HPLC conditions as per Example 2, except: Solvent A=$H_2O$/0.1% ammonium acetate and Solvent B=ACN. Yield 291 mg (55%) of pure material. Found m/z: 988.6, expected $MH_3^{3+}$ 987.7.

Example 4: Synthesis of Compound 3B from Compound 1

Step (a): Deprotection of Compound 1 to Give Compound 2

Compound 1 (7 mg, 2.37 µM) in a 5-ml reaction vial was treated with water (10 µL) and trifluoroacetic acid (190 µL), and then immersed within a sealed vial in a sonic bath for 10 minutes. The aqueous TFA was then removed in vacuo (approximately 30 mins), and the residue reconstituted in citrate buffer (pH 2.6, 1.7 mL) and loaded onto an automated synthesizer cassette (FastLab™, GE Healthcare Ltd) at position 14.

Step (b) Synthesis and Purification of $^{18}$F-Benzaldehyde

[$^{18}$F]fluoride was produced using a GEMS PETtrace cyclotron with a silver target via the [$^{18}$O](p,n) [$^{18}$F] nuclear reaction. Total target volumes of 1.5-3.5 mL were used. The radiofluoride was trapped on a Waters QMA cartridge (pre-conditioned with carbonate), and the fluoride is eluted with a solution of Kryptofix$_{2.2.2}$ (4 mg, 10.7 µM) and potassium carbonate (0.56 mg, 4.1 µM) in water (804) and acetonitrile (3204). Nitrogen was used to drive the solution off the QMA cartridge to the reaction vessel. The [$^{18}$F]fluoride was dried for 9 minutes at 120° C. under a steady stream of nitrogen and vacuum. Trimethylammonium benzaldehyde triflate, [Haka et al, J. Lab. Comp. Radiopharm., 27, 823-833 (1989)] (3.3 mg, 10.5 µM), in dimethylsulfoxide (1.1 mL) was added to the dried [$^{18}$F]fluoride, and the mixture heated at 105° C. for 7 minutes to produce 4-[$^{18}$F]fluorobenzaldehyde. The labelling efficiency was 69±3% decay corrected.

The crude labelling mixture was then diluted with ammonium hydroxide solution and loaded onto an MCX+SPE cartridge (pre-conditioned with water as part of the FASTlab sequence). The cartridge was washed with water, dried with nitrogen gas before elution of 4-[$^{18}$F]fluorobenzaldehyde back to the reaction vessel in ethanol (1 mL). Approximately 13% (decay corrected) of [$^{18}$F]fluorobenzaldehyde remained trapped on the cartridge.

Step (c): Aldehyde Condensation with Amino-Oxy Derivative (Compound 2)

Compound 2 (5 mg, 1.8 µmol) was transferred to the FASTlab reaction vessel prior to elution of 4-[$^{18}$F]fluorobenzaldehyde is returned from the MCX+ cartridge. The mixture was then heated at 70° C. for 17 minutes). Analytical HPLC confirmed that the RCP of the Compound 3B product was 63±9%.

The crude reaction mixture was diluted with water (10 mL) and loaded onto preparative HPLC. A 10 mM ammonium acetate vs acetonitrile system gave complete separation between the 3 possible radioactive components of the crude reaction mixture, namely [$^{18}$F]fluoride ($T_R$=0.5 mins), [$^{18}$F]Compound 3B ($T_R$=6 mins) and 4-[$^{18}$F]fluorobenzaldehyde ($T_R$=9 mins). Recovery of radioactivity from the HPLC system was good, with a recovery efficiency of 97%. The purified product was obtained by collecting the around 6 mins retention time.

Example 5: HPLC Separation of "F-Labelled c-Met Cyclic Peptide from Unlabelled Peptide Compound 3A was prepared according to Example 3.
(i) Analytical HPLC Conditions.
Column: XBridge Shield RP 18 (4.6×50) mm, 2.5 µm,
Aqueous mobile phase A: 10 mM NH$_4$Ac (buffer) pH ca. 6.8;
Organic mobile phase B: Acetonitrile.
Column temperature: 25° C.
Flow: 1.2 ml/min.
Gradient:

| Minutes | 0 | 1 | 16 | 19 | 22 | 22.1 | 26 |
|---------|---|---|----|----|----|------|----|
| % B | 20 | 20 | 40 | 100 | 100 | 20 | 20 |

(ii) Preparative HPLC Conditions
  Column: XBridge Shield RP 18 (10×100) mm, 5 μm.
  Aqueous mobile phase A: 10 mM NH₄Ac (buffer) pH ca. 6.8;
  Organic mobile phase B: Ethanol (90%) Mobile phase A (10%).
  Column temperature: 25° C.
  Flow: 4 ml/min.
  Gradient:

| Minutes | 0 | 1 | 16 | 20 | 25 | 26 |
|---|---|---|---|---|---|---|
| % B | 15 | 15 | 40 | 100 | 100 | 15 |

(iii) Analytical and Preparative HPLC Results.

| Compound | Analytical HPLC Retention time (minutes) | Preparative HPLC Retention time (minutes) |
|---|---|---|
| aniline hydrochloride | 1.8 | 3 |
| fluorobenzaldehyde | 4.3 | 13 |
| Compound 2 | 4.8 | undefined |
| Peptide 1 | 5.1 | undefined |
| Compound 3A | 8.8 | 19 |

Example 6: Biodistribution of $^{18}$F-Labelled c-Met Peptide (Compound 3B) in Tumour-Bearing Nude Mice CD-1 male nude mice (ca. 20 g) were housed in individual ventilated cages, with ad libitum access to food and water. HT-29 cells (ATCC, Cat. no. HTB-38) were grown in McCoy's 5a medium (Sigma # M8403) supplemented with 10% fetal bovine serum and penicillin/streptomycin. Cells were split 1:3 two times a week, at 70-80% confluent using 0.25% trypsin and incubated in 5% $CO_2$ at 37° C. The mice were injected s.c under light gas anaesthesia (Isoflurane) with the HT-29 cell suspension at one site (nape of the neck) with a nominal dose of $10^6$ cells per injections in a volume of 100 μl using a fine bore needle (25 G). The tumours were then allowed to develop for 20 days, or until at least 200 mm³ in volume (for inclusion in the study). After the 20 day growth time, animals were injected with Compound 3B (0.1 ml, 1-5 MBq/animal) as an intravenous bolus via the tail vein. At various times post injection animals were euthanised, dissected and the following organs and tissues removed:

The tumour uptake was 2.3% id/g at 2 minutes, peaking at 30 minutes (3.8% id/g) then decreasing over time to 1.9% id/g at 120 mins pi. The overall retention within the tumour was 83%. There was reasonably rapid blood clearance over time (initial 2 minute blood was 9.2% id/g decreasing to 0.81% id/g at 120 mins pi). Key background tissue (e.g. lungs and liver) followed the blood clearance profile over time, with uptake at 120 min p.i. of 1.1% id/g (liver) and 1.56% id/g (lungs).

Example 7: Receptor Blocking Study of Compound 3B in Tumour-Bearing Nude Mice

The study of Example 6 was repeated with co-injection of 100 and 1000-fold excess of the non-radioactive analogue, Compound 3A (~1.5 μg and 15 μg excess per animal), with animals dissected at 120 minutes post injection. All animals in this study had a similar bodyweight (range of 25 to 30 g).

The data demonstrated that a statistically significant reduction ($p<0.01$) in tumour uptake of Compound 3B was achieved with 1000-fold excess unlabelled peptide (HT-29 tumour uptake fell from 1.9 to 1.1% id/g; a 40% reduction).

Example 8: Primate PET Imaging of Compound 3B

The biodistribution of Compound 3B in three female cynomolgus monkeys was measured by PET. Two tracer injections were performed at each occasion:
  (a) tracer alone (Compound 3B) 3 MBq/kg (base line study);
  (b) tracer 9 MBq/kg with co-injection of with 0.15 mg/kg of Compound 3A (blockade study) four hours after baseline injection.

The tracer was injected as a bolus dose in 1-3 mL followed by 1 mL saline.

Blood samples (0.2 ml) for radioactivity determination were taken at intervals out to 210 minutes after administration. In the dynamic studies regions of interest were drawn in bone, heart, kidney, lung, liver, and muscle. In the whole-body studies, regions of interest were drawn in bone, brain, colon, heart, kidney, lung, liver, muscle, pancreas, small bowel, spleen, and bladder. Time-activity data were generated expressed as standard uptake values (SUV).

Specific binding (~40%) was observed in rhesus monkey liver in vitro using frozen section autoradiography. Rhesus monkey muscle was not observed to have any specific binding. In vivo studies in cynomolgus monkey showed a rapid uptake in liver which was reduced by >40% after co-injection of 0.15 mg/kg of Compound 3A. No specific binding to muscle in vivo was observed.

Example 9: Automated Synthesis of Compound 3B Using SPE Purification

The synthesis of Example 4 was carried out using a FastLab™ (GE Healthcare Ltd) automated synthesiser apparatus and the cassette of the synthesizer was configured with reagents, syringes and SPE cartridges.

The QMA (quaternary methyl ammonium water treatment), MCX+(mixed cation exchange) and C2 (low hydrophobicity) SPE cartridges were all obtained from Waters.

During the FASTlab sequence the cartridges were (in tandem) conditioned with Ethanol. Immediately prior to use, the cartridges were primed with dilute (0.2% phosphoric acid). The crude reaction mixture was diluted with 1% phosphoric acid and loaded onto the SPE. The SPE was washed with water before the product was eluted in 6 mL water (80% ethanol), and the radiochemical purity (RCP) analysed by analytical HPLC.

The results, based on the starting amount of $^{18}$F-fluoride used, were as follows:

| Starting Activity (MBq) | End of Synthesis Yield (%) | RCP |
|---|---|---|
| 493 | 21 | >99% |
| 750 | 25 | >99% |
| 1,000 | 26 | >99% |
| 49,000 | 19 | 94% |
| 61,000 | 18 | 98% |
| 67,400 | 21 | 96% |

Example 10: Human Studies

Imaging with Compound 3B was studied in 6 human patients previously diagnosed with head and neck squamous cell carcinoma. The agent was well-tolerated (no adverse effects). 5 of the 6 patients had moderate/high uptake of the tracer, and 1 patient had low uptake (similar to contralateral side). This is consistent with the literature reports of 80% of such patients overexpressing c-Met.

What is claimed is:

1. A method of assisting in determining whether or not a patient previously diagnosed with cancer, is susceptible to anti-Met therapy, said method comprising:
   (i) administering an imaging agent which comprises an 18F-radiolabelled c-Met binding cyclic peptide to said patient;
   (ii) using positron emission tomography (PET) imaging at least one site of said cancer of said patient with the imaging agent of step (i);
   (iii) determining from the imaging of step (ii) whether or not there is elevated uptake of said imaging agent at said site;
   (iv) when step (iii) shows elevated uptake, said patient is susceptible to said anti-Met therapy;
   (v) when step (iii) shows no elevated uptake, said patient is not susceptible to said anti-Met therapy;
wherein said c-Met binding cyclic peptide is an 18 to 30-mer cyclic peptide of Formula I:

$$Z^1\text{-[cMBP]-}Z^2 \quad (I)$$

where:
cMBP is of Formula (II):

$$\text{-(A)}x\text{-Q-(A')}y\text{-} \quad (II)$$

where Q is the amino acid sequence (SEQ-1), (SEQ-2), or (SEQ-3):
wherein SEQ-1 is -$Cys^a$-$X^1$-$Cys^c$-$X^2$-Gly-Pro-Pro-$X^3$-Phe-Glu-$Cys^d$-Trp-$Cys^b$-Tyr-$X^4$-$X^5$-$X^6$-;
wherein SEQ-2 is Ser-$Cys^a$-$X^1$-$Cys^c$-$X^2$-Gly-Pro-Pro-$X^3$-Phe-Glu-$Cys^d$-Trp-$Cys^b$-Tyr-$X^4$- $X^5$-$X^6$;
wherein SEQ-3 is Ala-Gly-Ser-$Cys^a$-$X^1$-$Cys^c$-$X^2$-Gly-Pro-Pro-$X^3$-Phe-Glu-$Cys^d$-Trp-$Cys^b$-Tyr-$X^4$-$X^5$-$X^6$-Gly-Thr;
wherein $X^1$ is Asn, His or Tyr;
$X^2$ is Gly, Ser, Thr or Asn;
$X^3$ is Thr or Arg;
$X^4$ is Ala, Asp, Glu, Gly or Ser;
$X^5$ is Ser or Thr;
$X^6$ is Asp or Glu;
and $Cys^{a-d}$ are each cysteine residues wherein residues a and b as well as c and d are cyclised to form two separate disulfide bonds;
A and A' are independently any amino acid other than Cys, with the proviso that at least one of A and A' is present and is Lys;
x and y are independently integers of value 0 to 13, wherein [x+y]=1 to 13;
$Z^1$ is attached to the N-terminus of cMBP, and is H or $M^{IG}$;
$Z^2$ is attached to the C-terminus of cMBP and is OH, $OB^c$, or $M^{IG}$,
where $B^c$ is a biocompatible cation;
each $M^{IG}$ is independently a metabolism inhibiting group which is a biocompatible group which inhibits or suppresses in vivo metabolism of the cMBP peptide;
wherein $M^{IG}$ comprises at least one of N-acylated groups —NH(C═O)RG, carboxamide, tert-butyl ester, benzyl ester, cyclohexyl ester, amino alcohol or a polyethyleneglycol (PEG) building block;

wherein the acyl group —(C=O)RG has RG selected from the group consisting of $C_{1-6}$ alkyl, $C_{3-10}$ aryl groups and comprises a polyethyleneglycol (PEG) building block;

wherein cMBP is labelled at the Lys residue of the A or A' groups with $^{18}F$.

2. The method of claim 1, wherein Lys is the last residue of cMBP:

wherein:

z is an integer of value y−1 cMBP comprises only one Lys residue.

3. The method of claim 1, wherein $X^3$ is Arg.

4. The method of claim 1, wherein either $-(A)_x-$ or $-(A')_y-$ contain -Gly-Gly-Gly-Lys-.

5. The method of claim 4, where cMBP has the amino acid sequence (SEQ-7):

Ala-Gly-Ser-$Cys^a$-Tyr-$Cys^c$-Ser-Gly-Pro-

Pro-Arg-Phe-Glu-$Cys^d$-Trp-$Cys^b$-Tyr-Glu-

Thr-Glu-Gly-Thr-Gly-Gly-Gly-Lys.

6. The method of claim 1, where both $Z^1$ and $Z^2$ are independently $M^{IG}$, wherein $M^{IG}$ for $Z^1$ comprises N-acylated groups —NH(C=O)RG where the acyl group —(C=O)RG has RG selected from the group consisting of $C_{1-6}$ alkyl, $C_{3-10}$ aryl groups and comprises a polyethyleneglycol (PEG) building block; wherein $M^{IG}$ for $Z^2$ is carboxamide, tert-butyl ester, benzyl ester, cyclohexyl ester, amino alcohol or a polyethyleneglycol (PEG) building block.

7. The method of claim 6, where $Z^1$ is acetyl and $Z^2$ is a primary amide.

8. The method of claim 1, where the cancer is non-small cell lung cancer, colorectal cancer, gastric cancer, pancreatic cancer, head and neck cancer, ovarian cancer, breast cancer, melanoma, glioma or sarcoma.

9. The method of claim 8, where the cancer is non-small cell lung cancer, colorectal cancer or gastric cancer.

10. The method of claim 1, wherein anti-Met therapy for the patient is either initiated or continued when the determination step (iii) is that anti-Met therapy is suitable for the patient.

11. The method of claim 10, wherein said method comprises performing the imaging and determination of steps (ii) and (iii) respectively at one or more time intervals after initiation of said therapy.

12. The method of claim 1, wherein either the $-(A)_x-$ or $-(A')_y-$ groups contain -Gly-Ser-Gly-Lys-.

13. The method of claim 1, wherein either the $-(A)_x-$ or $-(A')_y-$ groups contain -Gly-Ser-Gly-Ser-Lys-.

* * * * *